United States Patent [19]

Walker, Jr.

[11] 4,226,241

[45] Oct. 7, 1980

[54] SURGICAL FORCEPS

[76] Inventor: William E. Walker, Jr., 9th St. & Sugar Estate Rd., St. Thomas, V.I. 00801

[21] Appl. No.: 52,194

[22] Filed: Jun. 26, 1979

Related U.S. Application Data

[63] Continuation of Ser. No. 831,221, Sep. 7, 1977, abandoned, which is a continuation-in-part of Ser. No. 706,847, Jul. 19, 1976, abandoned.

[51] Int. Cl.³ .............................................. A61B 17/28
[52] U.S. Cl. ................................................... 128/321
[58] Field of Search ............... 128/321, 322, 325, 340, 128/346, 335, 339.5

[56] References Cited

U.S. PATENT DOCUMENTS

| | | | |
|---|---|---|---|
| 1,852,542 | 4/1932 | Sovatkin | 128/321 X |
| 2,618,268 | 11/1952 | English | 128/321 |
| 2,842,132 | 7/1958 | Soltero et al. | 128/322 |
| 2,887,111 | 5/1959 | Diaz | 128/321 |

FOREIGN PATENT DOCUMENTS

| | | | |
|---|---|---|---|
| 20743 | 7/1905 | Fed. Rep. of Germany | 128/321 |
| 524920 | 4/1931 | Fed. Rep. of Germany | 128/325 |
| 378427 | 10/1907 | France | 128/321 |

OTHER PUBLICATIONS

*Codman* General Surgical Instruments, p. 168, (1973).
*Sklar* Gynecological and Obstetrical Instruments.
McElmoyle W. A. "Two New Gastrectomy Clamps" Lancet 265 6778, 169, (1953).
Ross H. J. "An Intestinal Holding Clamp for Deep Pelvic Anastomosis of the Colon" Surg., Gyn. & Obs. 97²:248–249, 1953.
Abreu et al. "New Forceps for Retropubic Prostatectomy" Jour. of Urology 107:626, Apr. 1972.

*Primary Examiner*—Robert W. Michell
*Assistant Examiner*—Michael H. Thaler

[57] ABSTRACT

Surgical forceps comprising cross members having a pair of gripping arms pivotally connected to a pair of clamping arms which terminate with a pair of slightly curved, serrated mating jaws having aligned notches disposed on their outer surfaces to accommodate a needle for sutures. The pair of mated jaws are disposed in a plane substantially perpendicular to the plane containing the gripping arms.

4 Claims, 4 Drawing Figures

U.S. Patent     Oct. 7, 1980     4,226,241
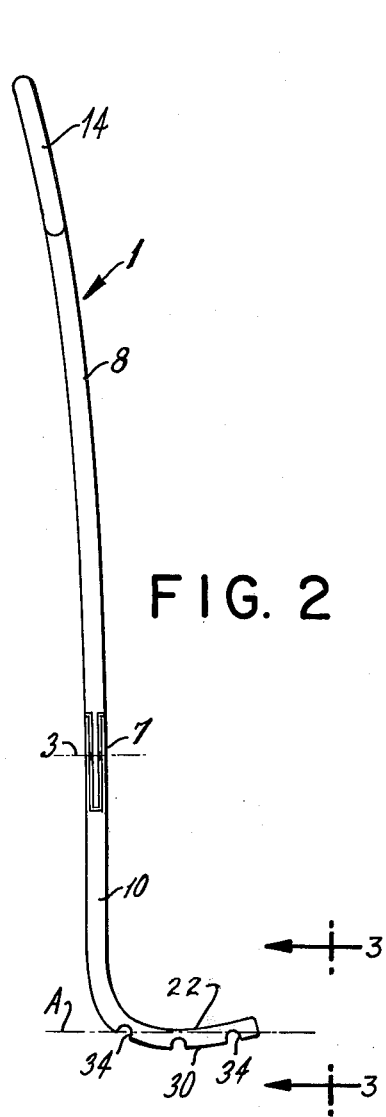
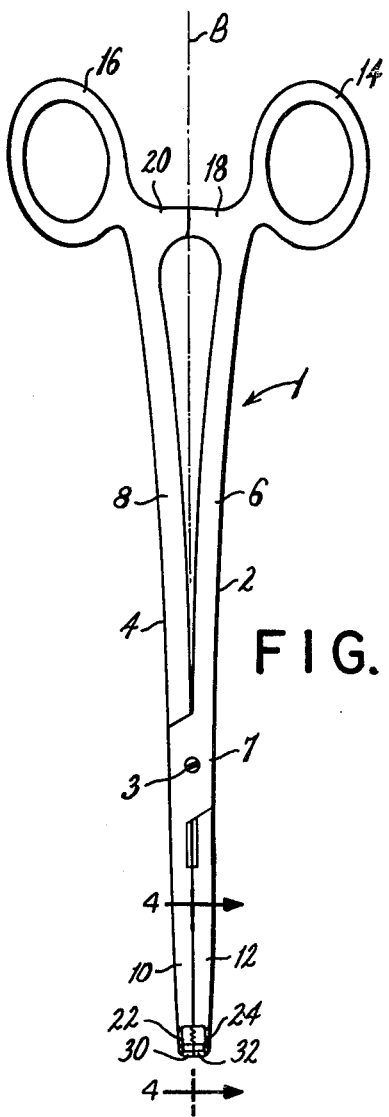
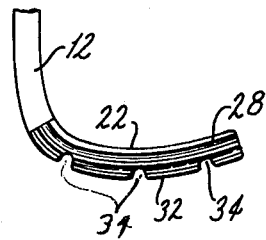
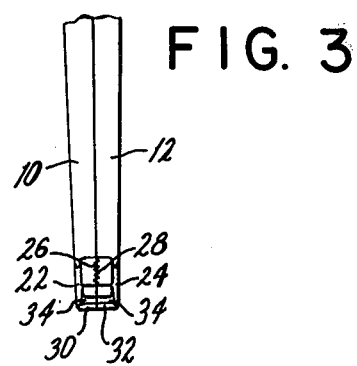

SURGICAL FORCEPS

This application is a continuation of our prior U.S. application Ser. No. 831,221 filed Sept. 7, 1977 now abandoned which in turn is a continuation-in-part of Ser. No. 706,847 filed July 19, 1976, now abandoned.

FIELD OF THE INVENTION

This invention relates to a surgical forceps and specifically to a manual vaginotomy clamp for use in surgical operations and specifically abdominal hysterectomy to more effectively separate and exterpate the uterus from the vagina.

BACKGROUND OF THE INVENTION

In the surgical procedure known as abdominal hysterectomy, the uterus is exterpated from the vagina at the junction of the two elements. This entails the partial clamping of the junction of the uterus and the vagina and then the excising of the uterus in a simple cutting operation or performing a plurality of cutting steps until the uterus is completely severed. Usually these operations involve inexact severing of the uterus which leaves a ragged edge, i.e., redundant tissue on the vaginal cuff. Despite the use of conventional clamps affixed on the edges of the vagina, the vaginal cuff is quite vascular and generally results in moderately profuse bleeding from the ragged edges, especially at the lateral angles of the vagina. The combination of the ragged edges of the vaginal cuff and tendency towards bleeding can result in the direct contamination of the vaginal cuff with vaginal bacterial flora, thus possibly resulting in the following major post-operative problems:

1. The infection and abscess of the vaginal cuff, and
2. Hemorrhage from the vaginal cuff usually within eight to fourteen days after the surgical operation.

Another drawback with using conventional type clamping means is that the inexact severing of the uterus could result in the removal of too little or too much of the vaginal edges anteriorly or posteriorly.

U.S. Pat. No. 2,887,111 discloses a surgical forceps having uneven jaws so that one of the jaws extends with a projection which possesses an eye as in a sewing needle through which an appropriate thread may be passed for the tying or binding of veins or the like.

U.S. Pat. No. 2,842,132 discloses a surgical clamp having relatively thin jaw sections with teeth therein for gripping a relatively small blood vessel longitudinally thereof. The jaw sections of the surgical clamp have interlocking fixation means to prevent scissoring or shifting of the jaw sections relative to each other while applying clamping pressure to the jaw sections for bringing the walls of a portion of a blood vessel into contact with each other.

U.S. Pat. No. 1,852,542 discloses a scissor-type surgical clamp having a mortise joint between the crossing portions of the clamp and having means for adjusting the clamp to tighten or loosen the connection between the crossed portions so that true alignment between the jaws or working points of the instrument may be effectively maintained.

French Pat. No. 378,427 discloses a scissor-type surgical clamp having affixed to pivoted means a pair of extended curved members disposed in a plane containing a pair of gripping members extending in the opposite direction from the securing means. The curved members have spaced apart edge slots which can be used to accommodate a needle for sutures.

In an article titled "New Forceps For Retropubic Prostatectomy" appearing in the Journal of Urology, 107:626, April 1972, a forceps is disclosed in which one of its extended jaws has four keyholes to receive sutures.

It is an object of the present invention to provide forceps for use in surgical operations which has hemostastosis means and appropriately spaced-apart grooves or notches for accommodating a needle for sutures.

Another object of the present invention is to provide surgical forceps having extended jaws which substantially conform to the anatomical curve of the cervix.

Another object of the present invention is to provide surgical forceps having a pair of extended jaws adapted to provide a crushing action so as to instantly provide hemostasis through the entire width of the body organ contained within the jaws.

Another object of the present invention is to provide surgical forceps that can be used in place of a plurality of conventional clamps presently being employed in certain surgical operations, such as abdominal hysterectomy.

Another object of the present invention is to provide surgical forceps that will expedite and shorten the surgical time required for abdominal hysterectomy.

Another object of the present invention is to provide surgical forceps which comprise few and simple parts and which will be easy to manipulate for use in surgical operations.

The foregoing and additional objects will become more fully apparent from the following description and the accompanying drawings.

SUMMARY OF THE INVENTION

The invention relates to surgical forceps comprising a pair of cross members having securing means for pivotally securing the members to one another, said cross members having a first set of arms extending in a first direction from the securing means and a second set of arms secured to said first set of arms and extending in an opposite direction from said securing means, said first set of arms adapted with gripping means for pivoting said arms about the securing means, the second set of arms extending in a plane parallel with the plane containing the first set of arms and terminating with a set of mating, preferably slightly curved, jaws extending in a plane substantially perpendicular to the plane containing the first set of arms and the securing means, and wherein the outer edge of each of the extending jaws has spaced-apart notches oriented such that when the jaws are in a closed mated position the notches are in alignment.

Preferably the mating surfaces of the jaws of the surgical forceps should be serrated, i.e., a formation resembling the toothed edge of a saw and disposed such that when the forceps are in the closed position, the toothed edge surface of one jaw will mate within the toothed edge surface of the other jaw. The serration can be extended across the width of the jaws or extended lengthwise of the jaws. Thus, when the forceps are pivoted toward the closed position, the serrated surfaces will provide a crushing action on the body organ contained therebetween which will effect hemostasis through the entire width of the organ within the jaws.

The extended jaws may be appropriately curved to conform to the anatomical curve of the cervix so that when the forceps are used, an almost instant hemostasis can be provided through the entire width of the vaginal cuff with a simple crushing action imparted through a closing of the forceps.

The outer edge of each of the jaws has notches, e.g., U-shaped, that are sufficiently spaced apart so that sutures can be placed in a body organ held between the jaws. When the surgical forceps are for use in abdominal hysterectomy operations, the notches can be spaced apart between about ⅜ and about ¾ inch, preferably about 9/16 inch. For abdominal hysterectomy applications, three spaced apart notches will generally be sufficient for effective suturing of the vagina.

The present invention will become more apparent from the following description thereof when considered together with the accompanying drawings which are set forth as being exemplary of embodiments of the present invention and are not intended, in any way, to be limitative thereof and wherein:

FIG. 1 is a front view of surgical forceps of this invention.

FIG. 2 is a side view of the surgical forceps as shown in FIG. 1.

FIG. 3 is an enlarged front view of the mating jaws of the surgical forceps as shown in FIG. 2 from line 3—3.

FIG. 4 is an inner side view of one of the jaws of the surgical forceps as shown in FIG. 1 through line 4—4.

Referring in detail to FIGS. 1 and 2, there is shown surgical forceps 1 comprising a pair of cross members 2, 4 pivoted to one another by pivotal connection 7 such as with a box or mortise joint type with a rivet or pivot pin 3 extending through the joint. Each of the cross members 2, 4 comprise arms 6 and 8, respectively, extending from the pivotal connection means 7 in one direction and arms 10 and 12, respectively, extending from the pivotal connection means 7 in an opposite direction. Arms 6 and 8 terminate with looped handle portions 14 and 16, respectively, for receiving a user's fingers for pivoting arms 6 and 8 about pivotal connection 7. As shown in FIGS. 1 and 2, the pivotal connection 7 is located at the rearward portion of arms 6 and 8 so as to substantially be in the plane therewith. As stated above, arms 6 and 8 have looped handle portions 14 and 16 respectively, so that the user can operate the forceps in a conventional manner, and as in all instruments of this type, the arms possess catches 18 and 20, respectively, forming a broach for maintaining the forceps in a closed position after crushing a part of an organ between jaws 22 and 24 as discussed hereinafter.

Arms 10 and 12 extend from pivotal connection 7 and terminate with slightly curved mating jaws 22 and 24, respectively, which lie in a plane substantially perpendicular to the plane containing arms 6 and 8 and pivotal connection 7 as shown by FIGS. 1 and 2.

Preferably, the longitudinal axis A of the jaws 22 and 24 as shown in FIG. 2 should be disposed at an angle of between about 70° to 110°, more preferably about 90°, from the longitudinal axis B of arms 6 and 8 as shown in FIG. 1. As shown in FIGS. 3 and 4, the mating jaws 22 and 24 have longitudinal serrations 26 and 28, respectively, which are disposed such that in the closed position, the serrations 26 of arm 10 are offset so as to fully mate with the serrations 28 in arm 12. Thus when the arms 6 and 8 are pivoted to the closed position, the jaws 22 and 24 are brought into a mating position which will be sufficient to crush and thereby provide an almost instant hemostasis through the body organ clamped therebetween. Although the serrations are shown only on the inner jaw surfaces, the serrations may continue further up arms 10 and 12, if desired. In addition, the serrations may be disposed widthwise of jaws 22 and 24, if desired.

As shown in FIGS. 1 and 2, the outer edges 30 and 32 of jaws 22 and 24, respectively, have three spaced-apart notches 34. In the closed position, notches 34 in jaw 22 will be in alignment with notches 34 in jaw 24 so as to provide slots to accommodate a needle for suturing a body organ confined and secured between the jaws. As shown in FIGS. 1 and 2, the user, such as a surgeon, can grasp the forceps by the looped members and by conventional pivoting can open and close the jaws of the forceps. By having the jaws of the forceps oriented approximately 90° to the gripping arm members, the user can squeeze a body organ between the jaws thereby exposing the squeezed area without having the gripping arm obscuring or blocking the view and access to said squeezed area.

When using the surgical forceps of this invention in an abdominal hysterectomy operation, the forceps clamp the uterus at its cervical end and squeeze it down so as to force the lower aspect of the uterus (hereinafter referred to as cervix) cephalad or upwards. Three sutures are then placed through the notches in the jaws of the forceps to secure the vaginal cuff. The cervis uteri can then be excised in one step without leaving redundant or uneven vaginal edges at the vaginal junction. The surgical forceps of this invention serve to provide excellent hemostasis by its crushing action of the vaginal cuff secured between the jaws of the forceps and also provide a seal against vaginal contamination as it effectively closes off the entire vagina. The use of the surgical forceps as a single clamp during the operation will not obscure the area of the uterus being excised. The surgical forceps of this invention can effectively shorten the time of excising the cervis uteri from the vagina from 15 to 30 minutes. This reduction in operating time can materially benefit the patient by shortening anesthetic time which can be most important in the marginally healthy patient who requires abdominal hysterectomy.

It is to be understood that other modifications and changes to the preferred embodiment of the invention herein shown and described can also be made without departing from the spirit and scope of the invention.

What is claimed is:

1. Surgical forceps comprising a pair of cross members having securing means for pivotally securing the cross members to one another, said cross members having a first set of arms extending in a first direction from the securing means and a second set of arms secured to said first set of arms and extending in an opposite direction from said securing means, said first set of arms adapted with gripping means for pivoting said arms about the securing means, the second set of arms terminating with a set of equal length mating jaws extending in a plane substantially perpendicular to the plane containing the first set of arms and curved to the anatomical curve of the cervix and wherein the outer edge of each of the extending jaws has three spaced apart notches oriented such that when the jaws are in a closed mated position the jaws are disposed in parallel planes with the notches in abutting alignment, and said notches in each jaw being spaced apart from an adjacent notch by between about ⅜ and about ¾ inch.

2. The surgical forceps of claim 1 wherein the inner surface of each jaw is serrated and offset with respect to the serrations in the surface of the other jaw so that in the closed position of the forceps, the serrated surfaces of the jaws will mate in a closed position.

3. The surgical forceps of claim 2 wherein the serrations are oriented lengthwise on the inner surface of each jaw.

4. The surgical forceps of claim 2 wherein the serrations are oriented widthwise on the inner surface of each jaw.

* * * * *